United States Patent
Li et al.

(10) Patent No.: US 10,973,455 B2
(45) Date of Patent: Apr. 13, 2021

(54) HEART RATE VARIABILITY ANALYSIS METHOD, DEVICE AND USE THEREOF

(71) Applicants: TSINGHUA UNIVERSITY, Beijing (CN); BEIJING PINS MEDICAL CO., LTD, Beijing (CN)

(72) Inventors: Luming Li, Beijing (CN); Hongyun Liu, Beijing (CN); Zhao Yang, Beijing (CN)

(73) Assignees: BEIJING PINS MEDICAL CO., LTD, Beijing (CN); TSINGHUA UNIVERSITY, Beijing (CN)

( * ) Notice: Subject to any disclaimer, the term of this patent is extended or adjusted under 35 U.S.C. 154(b) by 200 days.

(21) Appl. No.: 16/086,399

(22) PCT Filed: Aug. 4, 2017

(86) PCT No.: PCT/CN2017/095953
§ 371 (c)(1),
(2) Date: Sep. 19, 2018

(87) PCT Pub. No.: WO2018/099120
PCT Pub. Date: Jun. 7, 2018

(65) Prior Publication Data
US 2019/0099121 A1 Apr. 4, 2019

(30) Foreign Application Priority Data
Dec. 2, 2016 (CN) .......................... 201611094149.6

(51) Int. Cl.
*A61B 5/024* (2006.01)
*A61B 5/00* (2006.01)
(Continued)

(52) U.S. Cl.
CPC ........ *A61B 5/4094* (2013.01); *A61B 5/02405* (2013.01); *A61B 5/4035* (2013.01);
(Continued)

(58) Field of Classification Search
CPC ....... A61B 5/40; A61B 5/4029; A61B 5/4035; A61B 5/4058; A61B 5/4076;
(Continued)

(56) References Cited

U.S. PATENT DOCUMENTS 6,045,513 A * 4/2000 Stone .................. A61B 5/0031
600/508
7,819,814 B2 * 10/2010 Gavriely ............ A61B 5/02405
600/528
(Continued)

FOREIGN PATENT DOCUMENTS

CN 105147248 A 12/2015
CN 105769222 A 7/2016
(Continued)

OTHER PUBLICATIONS

Fred Shaffer and J. P. Ginsberg; An Overview of Heart Rate Variability Metrics and Norms (Year: 2017).*
(Continued)

*Primary Examiner* — Ahmed M Farah
(74) *Attorney, Agent, or Firm* — Grossman, Tucker, Perreault & Pfleger, PLLC

(57) ABSTRACT

A method and an apparatus for analyzing heart rate Variability (HRV), and use thereof are provided. A low-cost, portable and wearable signal acquisition device is utilized to acquire electrocardiography (ECG) signals of epilepsy patients for 24 hours before treatment, and a time domain index, a frequency domain index and a nonlinear index of the ECG during a long term and during a short term are calculated with a programmed HRV analysis method, and the efficacy of vagus nerve stimulation (VNS) treatment for patients with medically intractable epilepsy is accurately and efficiently predicted based on characteristic parameters for characterizing an effect level of the vagus nerve regulating the heart rate, i.e., vagus nerve activity, thereby avoiding
(Continued)

unnecessary costs and avoiding the delay of the optimal treatment timing. In addition, the characteristic parameters obtained by the HRV analysis on the ECG may be utilized to clearly select VNS treatment indication patients.

3 Claims, 5 Drawing Sheets

(51) Int. Cl.
| | | |
|---|---|---|
| *A61B 5/0245* | (2006.01) | |
| *A61B 5/316* | (2021.01) | |
| *A61B 5/339* | (2021.01) | |
| *A61B 5/341* | (2021.01) | |
| *A61B 5/349* | (2021.01) | |
| *A61B 5/352* | (2021.01) | |

(52) U.S. Cl.
CPC .......... *A61B 5/4848* (2013.01); *A61B 5/0245* (2013.01); *A61B 5/316* (2021.01); *A61B 5/339* (2021.01); *A61B 5/341* (2021.01); *A61B 5/349* (2021.01); *A61B 5/352* (2021.01)

(58) Field of Classification Search
CPC ....... A61B 5/4094; A61B 5/4848; A61B 5/04; A61B 5/04001; A61B 5/04004; A61B 5/04012; A61B 5/04014; A61B 5/0402; A61B 5/04021; A61B 5/04023; A61B 5/0452; A61B 5/0456; A61B 5/0468; A61B 5/024; A61B 5/02405; A61B 5/0245; A61B 5/0255
USPC .......... 600/508, 509, 513, 515–519; 128/898
See application file for complete search history.

(56) References Cited

U.S. PATENT DOCUMENTS

| | | | | |
|---|---|---|---|---|
| 2009/0275849 | A1* | 11/2009 | Stewart | A61B 5/0456 600/518 |
| 2010/0113865 | A1* | 5/2010 | Chung | A61M 21/02 600/27 |
| 2012/0179055 | A1* | 7/2012 | Tamil | A61B 5/7465 600/509 |
| 2013/0253353 | A1 | 9/2013 | Kawamura | |

FOREIGN PATENT DOCUMENTS

| | | |
|---|---|---|
| CN | 105796096 A | 7/2016 |
| CN | 106551691 A | 4/2017 |

OTHER PUBLICATIONS

Lotufo, P.A. et al., "A systematic review and meta-analysis of heart rate variability in epilepsy and antiepileptic drugs", Epilepsia, 2012, p. 272-282, vol. 53; 11 pgs.

Evrengul, H. et al., "Time and frequency domain analyses of heart rate variability in patients with epilepsy", Epilepsy Research, 2005, p. 131-139, vol. 63; 9 pgs.

Galli, R. et al., "Analysis of RR variability in drug-resistant epilepsy patients chronically treated with vagus nerve stimulation", Autonomic Neuroscience: Basic and Clinical, 2003, p. 52-59, vol. 107; 8 pgs.

International Search Report dated Sep. 30, 2017 of corresponding International application No. PCT/CN2017/095953; 6 pgs.

* cited by examiner

HEART RATE VARIABILITY ANALYSIS METHOD, DEVICE AND USE THEREOF

FIELD

The present disclosure relates to a method and an apparatus for analyzing heart rate variability, and use thereof, and in particular to prediction for an efficacy of vagus nerve stimulation (VNS) treatment for medically intractable epilepsy with the method and the apparatus for analyzing the heart rate variability.

BACKGROUND

Epilepsy as a disease affects the lives of patients. Most patients can control the seizure with one or more drugs in a combination manner. However, some patients are not sensitive to drug treatment, which are referred to as patients with medically intractable epilepsy. The vagus nerve stimulation (VNS) as an auxiliary treatment method can effectively control the epileptic seizures in patients with medically intractable epilepsy, but individual differences in efficacy are great and have high uncertainties. It is found from the statistical analysis that, epileptic seizures in only 5% to 9% of patients with medically intractable epilepsy who have received the VNS treatment can be controlled completely, while about 10% of patients have no change in epileptic seizures after receiving the VNS treatment, and epileptic seizures in other patients may be decreased to some extent. In general, epileptic seizures in 50% to 60% of the patients with medically intractable epilepsy who have received the VNS treatment can be decreased by 50%. In view of the uncertainty and individual differences in the efficacy of the VNS treatment for medically intractable epilepsy, researchers have been trying to screen out patients suitable for the VNS treatment by evaluation before treatment.

There is no clear and quantified method for predicting the efficacy of the VNS treatment for medically intractable epilepsy in clinical practice. The related factors of VNS efficacy have been studied based on electroencephalography (EEG), magnetic resonance imaging (MRI), and patient demographic characteristics (including gender, age, and the like), clinical history (disease course), seizure characteristics (including seizure type, seizure frequency, lesion location, and the like), and the studied conclusions are inconsistent or even contradictory with each other.

In the conventional technology, as shown in FIG. 1, a systematic and comprehensive preoperative evaluation (including analysis on demographic characteristics, clinical history, seizure characteristics, MRI, EEG, and the like) is firstly required to be performed on patients with medically intractable epilepsy before the VNS treatment, and then the VNS implantation treatment is performed. When two weeks has elapsed after the treatment, the stimulation parameters are gradually regulated in accordance with performances and technical characteristics of the VNS product, based on specific responses of the patients to VNS acute stimulation, and the seizures in the patients are recorded regularly. After the corresponding follow-up period (which is generally set as one year), the patients are classified based on the reduction of seizures, that is, the efficacy. Finally, the preoperative evaluation data for the patient groups with different efficacies is statistically analyzed to find a parameter with statistical differences between the patient groups with different efficacies, so as to serve as a sensitive factor in predicting the efficacy of the VNS treatment for medically intractable epilepsy.

The existing methods based on EEG and MRI have disadvantages of high cost, complicated operation, and high requirements on the professional knowledge of analysts. Overall, studies based on the above methods have not been applied in clinical practice due to the studied conclusions for a same problem being inconsistent or even contradictory with each other. According to the method based on the 24-hour dynamic electrocardiography signal proposed in the present disclosure, a subject is only required to wear a portable dynamic electrocardiography recording box to acquire the ECG in a free movement state of the subject, which results in simple operations. General hospitals charge outpatients 240 yuan for the 24-hour dynamic electrocardiography examination, and the cost is lower compared with about 1,000 yuan of the long-term video electroencephalography and magnetic resonance imaging examination. Due to the 24-hour dynamic electrocardiography acquisition being not limited by activities, the acquisition is simpler and the consistency is better compared with the methods based on the EEG and MRI.

The heart rate variability (HRV) refers to a change in an interval between adjacent heart beats in an electrocardiography (ECG) signal with time. The HRV is generated caused by the regulation of an autonomic nervous system on sinus node automaticity, which makes the heart beat intervals have tens of milliseconds or even greater differences or fluctuations. Since the HRV contains a large amount of information on the neurohumoral regulation, the HRV is a quantitative, non-invasive and repeatable index for indicating the activity and regulation functions of the autonomic nervous system in a cardiovascular system. The HRV analysis may indirectly reflect interactions between sympathetic and parasympathetic nerves.

At present, there is no study and technical solution for predicting the efficacy of the VNS treatment for medically intractable epilepsy by the HRV analysis technology based on the ECG. Since the epileptic disease is related to the cardiac autonomic dysfunction, the autonomic nervous system balance of the patient is broken with the epilepsy seizure and progression, which generally results in the increased sympathetic nerve activity and decreased vagus nerve activity. Based on this, in the present disclosure, a low-cost, portable and wearable signal acquisition device is utilized to acquire ECG signals of epilepsy patients for 24 hours before treatment, a time domain characteristic parameter, a frequency domain characteristic parameter and a nonlinear characteristic parameter of the ECG are calculated with a programmed HRV analysis method, and characteristic parameters for characterizing the vagus nerve activity are selected to accurately and efficiently predict the efficacy of the VNS treatment for medically intractable epilepsy.

SUMMARY

It is found that, the epileptic disease is related to the cardiac autonomic dysfunction, and the autonomic nervous system balance of the patient is broken with the epilepsy seizure and progression, which generally results in the increased sympathetic nerve activity and decreased vagus nerve activity. In addition, it is found that heart rate variability (HRV) is an important index. The HRV refers to a change in an interval between adjacent heart beats in an electrocardiography (ECG) signal with time. The HRV is generated caused by the regulation of an autonomic nervous system on sinus node automaticity, which makes the heart beat intervals have tens of milliseconds or even greater differences or fluctuations. Since the HRV contains a large amount of information on the neurohumoral regulation, the HRV is a quantitative, non-invasive and repeatable index for indicating the activity and regulation functions of the autonomic nervous system in a cardiovascular system. The HRV analysis may indirectly reflect interactions between sympathetic and parasympathetic nerves.

Based on above, in the present disclosure, a low-cost, portable and wearable signal acquisition device is utilized to acquire ECG signals of epilepsy patients for 24 hours before treatment, and a time domain characteristic parameter, a frequency domain characteristic parameter and a nonlinear characteristic parameter of the ECG during a long term and during a short term are calculated with a programmed HRV analysis method, and the efficacy of the VNS treatment for medically intractable epilepsy is accurately and efficiently predicted based on characteristic parameters for characterizing the vagus nerve activity in the autonomic nervous system, thereby avoiding unnecessary costs and avoiding the delay of the optimal treatment timing. In addition, the characteristic parameters for characterizing the vagus nerve activity obtained by the HRV analysis on the ECG may be utilized to clearly select VNS treatment indication patients, so that the overall efficacy of the VNS treatment can be improved.

A method for analyzing heart rate variability is provided, which includes the following steps:

1) acquiring electrocardiography data in vitro;
2) performing a digitization process and a denoising process on the electrocardiography data;
3) forming a sinus NN interval sequence with the processed electrocardiography data;
4) selecting sinus NN interval data during a long term and during short terms in an awake state and in a sleep state; and
5) calculating a time domain index, a frequency domain index and a nonlinear index for the sinus NN interval data during the long term and during the short terms in the awake state and in the sleep state (calculation formulas for the indexes are shown in tables below).

where RR is a time interval or an interval between two adjacent heart beats; N is the total number of RR intervals; and RRi is an i-th RR interval.

The frequency domain index may be explained as follows. It can be seen from the power spectrum analysis that, three separate spectrum peaks exist in a typical HRV power spectrum, and the three spectrum peaks are substantially located in a frequency band of 0.04 Hz, a frequency band of 0.1 Hz, and a frequency band having frequencies greater than 0.15 Hz, respectively. The area under each frequency band can be used as a power spectrum energy measurement, i.e., as a frequency domain index of the HRV. Since the frequency domain index reflects the regulation of the autonomic nervous system at the frequency bands, and the physiological factors are properly separated, the frequency domain index can accurately reflect the true situation of HRV and has a great clinical application value.

TABLE 2 frequency domain index

| Name of index | Definition of index | Unit | Frequency range | Meaning of index |
|---|---|---|---|---|
| TP | Total signal power, i.e., sum of VLF, LF and HF | $ms^2$ | ≤0.4 Hz | The index indicates a total variability in the signal |
| VLF | Power in very lower frequency band | $ms^2$ | 0.0033 to 0.04 Hz | Unknown mechanism, which may be related to long-term regulation mechanisms related to body temperature regulation, renin angiotensin system and humoral factors |
| LF | Power in lower frequency band | $ms^2$ | 0.04 to 0.15 Hz | The explanation is still controversial, but most scholars consider the index as being indicating sympathetic nerve activity |

TABLE 1 time domain index

| Name of index | Definition of index | Unit | Meaning of index |
|---|---|---|---|
| mean value (MEAN) | $MEAN = \overline{RR} = \sum_{i=1}^{N} RR_i / N$ | ms | The index indicates an average level of RR intervals |
| overall standard deviation (SDNN) | $SDNN = \sqrt{\frac{1}{N} \sum_{i=1}^{N} (RR_i - \overline{RR})^2}$ | ms | The index indicates an overall change in the HRV during a long term of 24 hours |
| root-mean-square of difference of adjacent interval (RMSSD) | $RMSSD = \sqrt{\frac{1}{N-1} \sum_{i=1}^{N-1} (RR_{i+1} - RR_i)^2}$ | ms | The index indicates a component that changes rapidly in the HRV |
| percentage of adjacent intervals with difference greater than 50 ms (pNN50) | $pNN50 = NN50/TotalNN \times 100\%$ | % | The index indicates a sudden change in the RR interval, and can sensitively reflect the vagus nerve activity |

TABLE 2-continued frequency domain index

| Name of index | Definition of index | Unit | Frequency range | Meaning of index |
|---|---|---|---|---|
| HF | Power in high frequency band | $ms^2$ | 0.15 to 0.4 Hz | The index indicates the vagus nerve activity, and reflects the respiratory variation. |
| LF/HF | Ratio of power in lower frequency band to power in high frequency band | — | — | The index indicates a balance state between a sympathetic nerve tension and a vagus nerve tension. |

The nonlinear index may be explained as follows. In recent years, great progress has been made in the study on nonlinear dynamics, which has aroused great interest in the fields of physics, chemistry, and information science. By describing and analyzing, with the nonlinear dynamic method, a complex process in which the autonomic nervous system controls and regulates the heart rate, more meaningful information can be obtained to improve the accuracy of the HRV as a prediction index. The HRV nonlinear index utilized in the present disclosure mainly includes SD1 and SD2 indexes in a Poincare Plot (as shown in FIG. 4). An NN interval is considered as a research object, and dispersion characteristics of a change between two adjacent NN intervals are displayed in the form of coordinates. Standard deviations on long and short axes at the center of the plot are measured, respectively. The standard deviation measured with the short axis as a central axis is referred to as SD1, which reflects differences between instantaneous heart beats. The standard deviation measured with the long axis as a central axis is referred to as SD2, which reflects differences between the NN intervals during a long time period.

DETAILED DESCRIPTION OF EMBODIMENTS

First Embodiment

Figure 1:
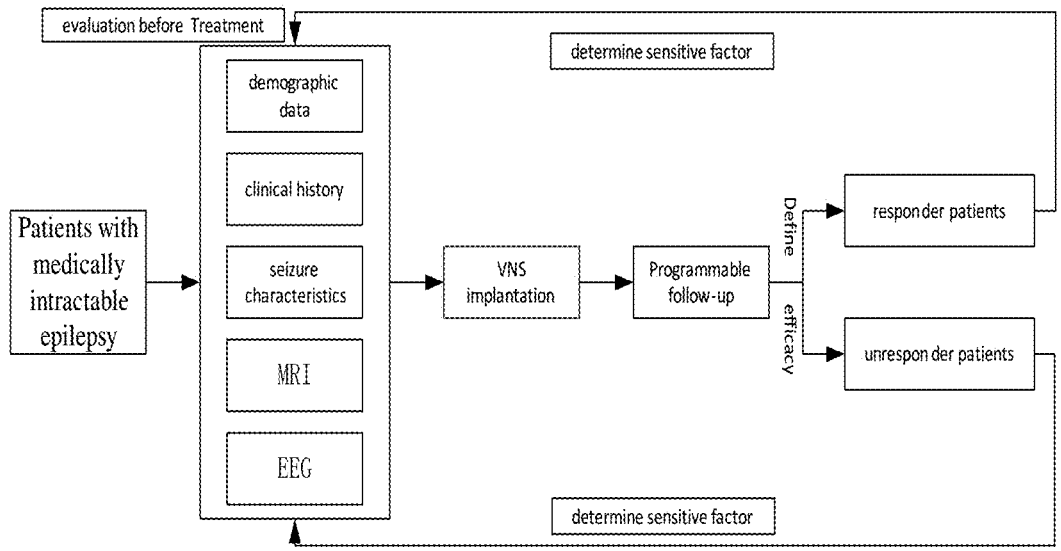
FIG. 1 is a flowchart of screening VNS indication patients in the conventional technology.
Figure 2:
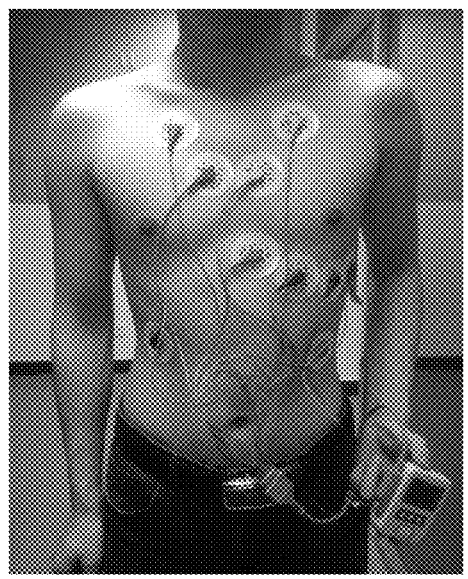
FIG. 2 is a schematic diagram showing 12-lead ECG acquisition.
Figure 3:
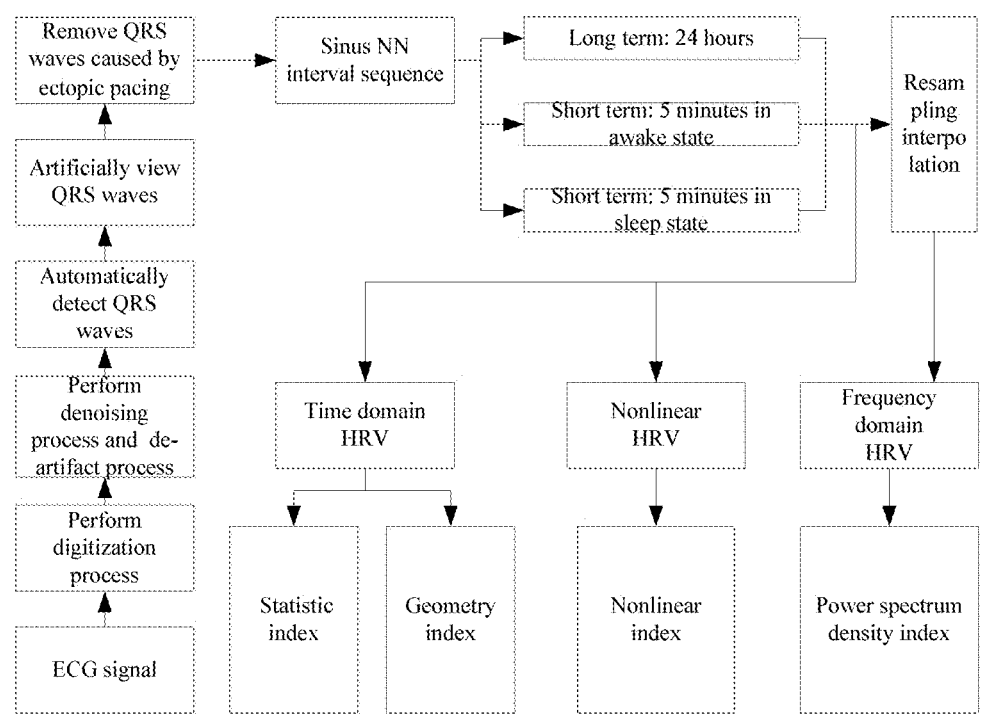
FIG. 3 is a flowchart of processing an ECG signal.
Figure 4:
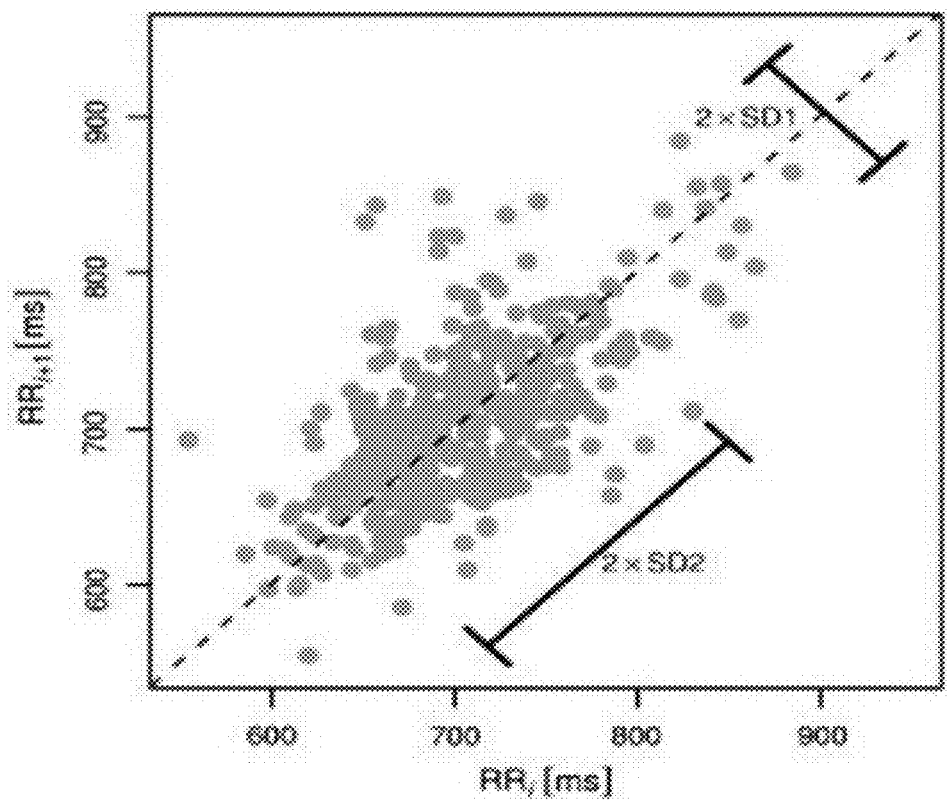
FIG. 4 is a schematic diagram showing calculation for HRV nonlinear indexes SD1 and SD2.

As shown in FIG. 2, standard 12-lead ECG acquisition is performed for 24 hours before treatment. In the acquisition process, an electrocardiography acquisition device is required to have a sampling frequency greater than or equal to 500 Hz. During the ECG recording, subjects should not make activities such as strenuous exercise and dose that may affect the cardiac function. The recording time period is set as 24 hours. Recording environments or conditions in which the subjects are located should be substantially similar to each other. In addition, it is required that data for HRV analysis is normal sinus NN interval data. In the HRV analysis, a time domain index, a frequency domain index and a nonlinear index not only during a time period of 24 hours, but also during short terms of 5 minutes in an awake state and in a sleep state are extracted. A specific flow of processing an ECG signal is as shown in FIG. 3, which includes:

1) acquiring an ECG signal and digitizing the signal;
2) performing a denoising process and a de-artifact process on the digitized signal;
3) automatically detecting QRS waves in the signal;
4) artificially viewing QRS waves in the detected signal;
5) removing QRS waves caused by ectopic pacing in the signal;
6) forming a sinus NN interval sequence;
7) selecting sinus NN interval data of each subject during a long term of 24 hours and during short terms of 5 minutes in an awake state and in a sleep state;
8) calculating, with the method as shown in Table 1, Table 2 and FIG. 4, a time domain index, a frequency domain index and a nonlinear index for the sinus NN interval data of the subject during the long term of 24 hours and during the short terms of 5 minutes in the awake state and in the sleep state; and
9) selecting characteristic parameters RMSSD, pNN50, SD1 and HF for characterizing vagus nerve activity.

Figure 5:
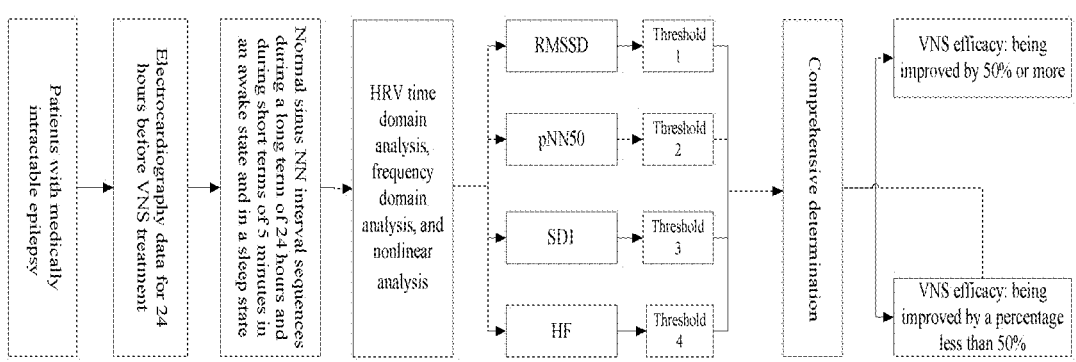
FIG. 5 is a flowchart showing a determining process.

The electrocardiography acquisition is performed on patients with medically intractable epilepsy for 24 hours before treatment. The electrocardiography data acquired during 24 hours is processed with the above method to obtain normal sinus NN interval sequences during the long term of 24 hours and during the short terms of 5 minutes in the awake state and in the sleep state. HRV time domain analysis, frequency domain analysis, and nonlinear analysis are performed on the NN interval sequences during the long term and the short terms with the method as shown in Table 1, Table 2 and FIG. 4, and characteristic parameters RMSSD, pNN50, SD1 and HF for characterizing vagus nerve activity are selected. Thresholds corresponding to the characteristic parameters are determined to make a comprehensive determination and selection, so as to predict and determine an efficacy of VNS treatment for medically intractable epilepsy (as shown in FIG. 5). The characteristic parameters RMSSD, pNN50, SD1, and HF for characterizing the vagus nerve activity during a time period of 5 minutes at night, are individually utilized to predict the efficacy of VNS treatment for medically intractable epilepsy, and the selected corresponding thresholds and corresponding prediction accuracies are described as follows.

The threshold for RMSSD is selected as 37 ms. That is, in a case that the ECG analysis result on a patient before treatment is greater than the threshold, the epileptic seizure after VNS treatment is decreased by 50% or more. In addition, the prediction accuracy is 88.2%. The threshold may also be utilized for screening patients.

The threshold for pNN50 is selected as 27%. That is, in a case that the ECG analysis result on a patient before treatment is greater than the threshold, the epileptic seizure after VNS treatment is decreased by 50% or more. In addition, the prediction accuracy is 82.7%. The threshold may also be utilized for screening patients.

The threshold for SD1 is selected as 35 ms. That is, in a case that the ECG analysis result on a patient before treatment is greater than the threshold, the epileptic seizure after VNS treatment is decreased by 50% or more. In addition, the prediction accuracy is 70.6%. The threshold may also be utilized for screening patients.

The threshold for HF is selected as 798 ms². That is, in a case that the ECG analysis result on a patient before treatment is greater than the threshold, the epileptic seizure after VNS treatment is decreased by 50% or more. In addition, the prediction accuracy is 76.5%. The threshold may also be utilized for screening patients.

Second Embodiment

In the HRV analysis method according to the first embodiment, other indexes that can characterize the vagus nerve activity may also be utilized to predict the efficacy of the VNS treatment for medically intractable epilepsy and screen patients.

According to the present disclosure, the ECG acquisition is performed on patients with medically intractable epilepsy for 24 hours before treatment, and the HRV time domain analysis, frequency domain analysis and nonlinear analysis are performed, so that the efficacy for the patients with medically intractable epilepsy can be predicted before VNS treatment, and the patients with medically intractable epilepsy can be correctly guided to determine whether to receive the VNS treatment, thereby avoiding unnecessary costs and avoiding the delay of the optimal treatment timing. In addition, the characteristic parameters for characterizing the vagus nerve activity obtained by the HRV analysis on the ECG are utilized to predict the efficacy of VNS treatment and clearly select VNS treatment indication patients, so that the overall efficacy of the VNS treatment can be improved.

Third Embodiment

Based on the above screening method, 32 patients with medically intractable epilepsy who have completed the VNS treatment at a Beijing Tiantan Hospital from Aug. 13, 2014 to Dec. 31, 2014 are selected for verification. A comprehensive evaluation (including analysis on demographic characteristics, clinical history, of antiepileptic drug history, video electroencephalography for 24 hours, MRI, and dynamic electrocardiography for 24 hours) is performed on the 32 patients with medically intractable epilepsy before the VNS treatment.

Figure 6:
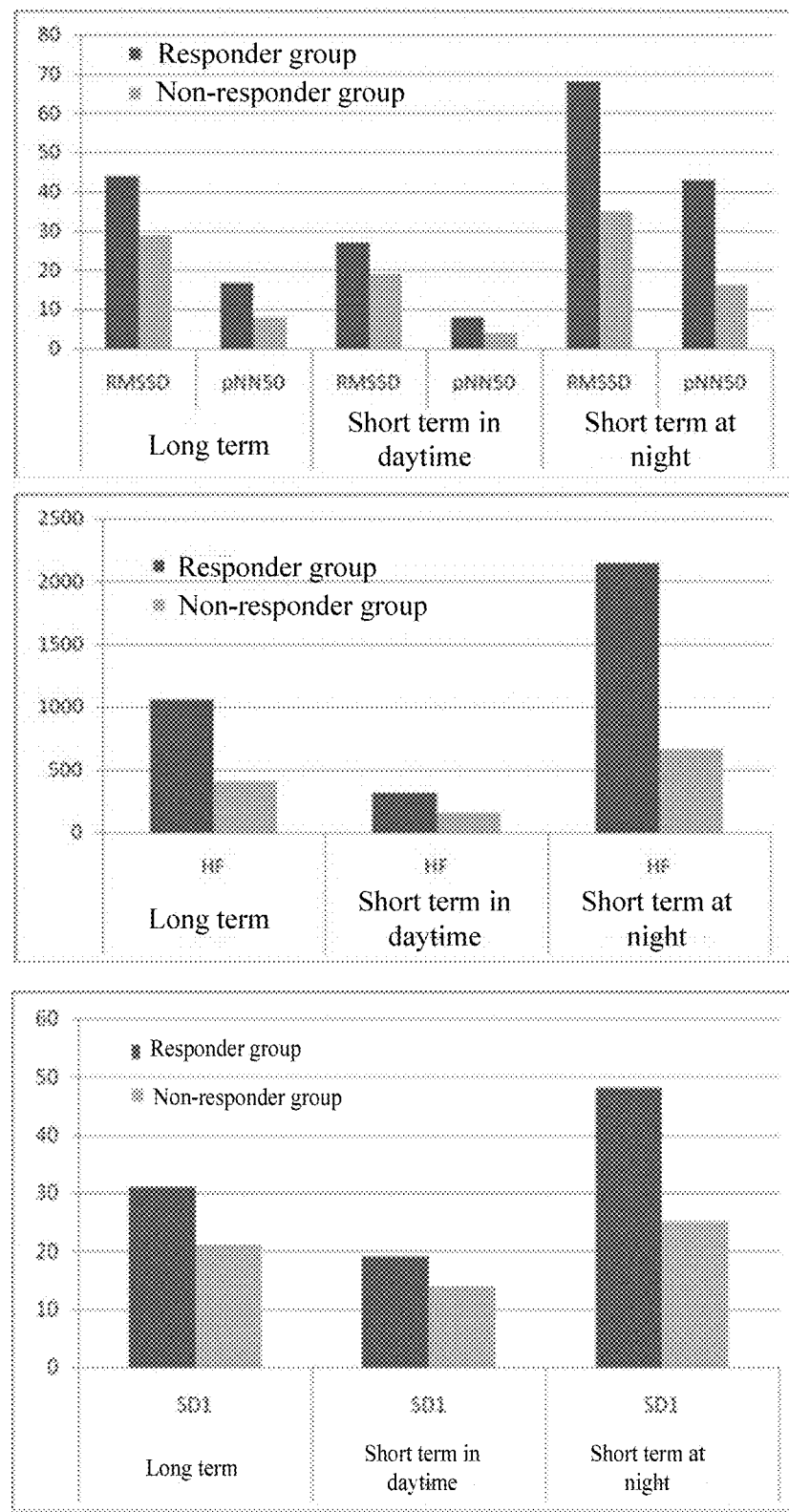
FIG. 6 is diagram showing parameters for a responder group Responder50 and a non-responder group Non-responder50.
Figure 7:
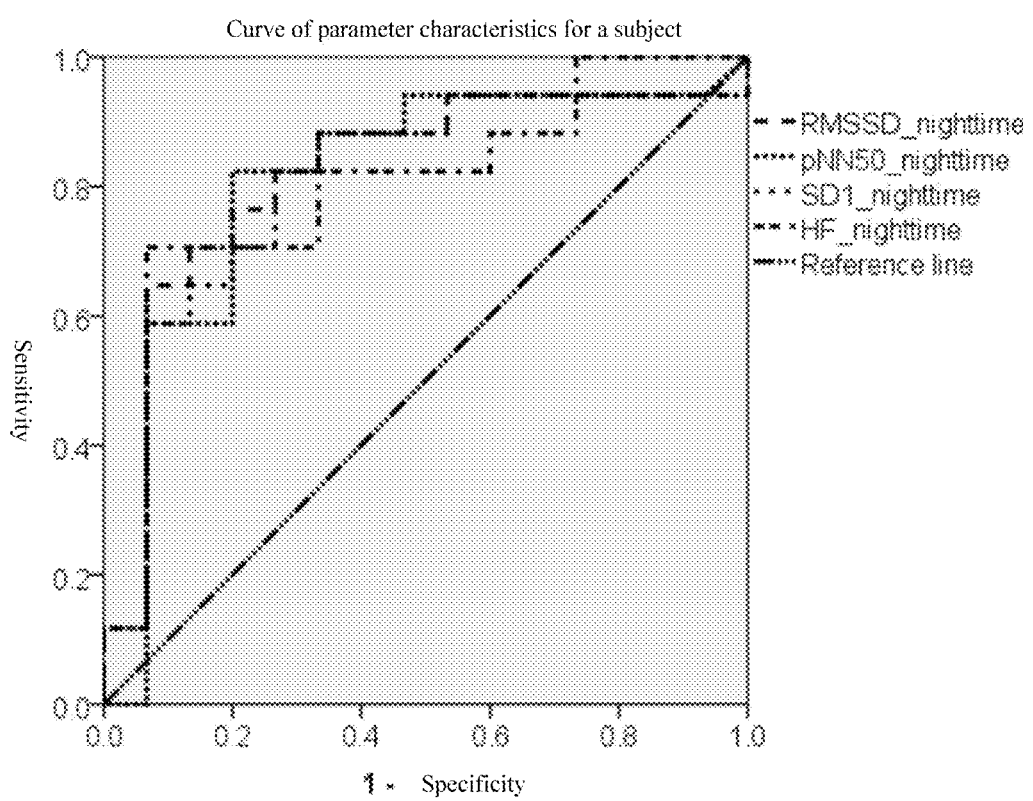
FIG. 7 is a curve showing parameter characteristics for a subject.

The HRV time domain analysis, frequency domain analysis, and nonlinear analysis are performed on the dynamic electrocardiography data for 24 hours before treatment with the ECG signal processing method described above, and the characteristic parameters RMSSD, pNN50, SD1, and HF that characterize the vagus nerve activity are extracted for each patient. It is found from the follow-up for one year after treatment that, among the 32 patients with medically intractable epilepsy who have received the VNS treatment, epileptic seizures in 17 patients (where epileptic seizures in 6 patients can be controlled completely) are decreased by 50% or more, which are referred to as a responder group Responder50, and epileptic seizures in other 15 patients (where 4 patients have no change in epileptic seizures after receiving the VNS treatment) are decreased by 50% or less, which are referred to as a non-responder group Non-responder50. The parameters RMSSD, pNN50, SD1 and HF for the responder group Responder50 and the non-responder group Non-responder50 are shown in FIG. 6. Since the parameters for characterizing the vagus nerve activity for the two groups of patients have significant statistically differences, it is indicated that, the efficacy of the VNS treatment is related to vagus nerve activity in patients before treatment, and the efficacy of the VNS treatment can be predicted with the HRV analysis method. Further, efficacy prediction abilities of RMSSD, pNN50, SD1 and HF during the long term of 24 hours and during the short terms of 5 minutes in the awake state and in the sleep state are evaluated. It is found from the ROC curve analysis that prediction of the RMSSD during the short term of 5 minutes in the sleep state is most accurate among the above four parameters (as shown in FIG. 7). In the case that the threshold for RMSSD is set as 37 ms, only 2 patients among the 17 patients in the responder group have RMSSD less than 37 ms, and the other patients all have RMSSD greater than 37 ms, and the prediction accuracy is over 85%. Therefore, it can be proved that the characteristics parameter for characterizing the vagus nerve activity obtained by the above HRV analysis can be utilized to predict the efficacy of VNS treatment accurately and effectively and screen the VNS indication patients.

The above description shows only preferred embodiments of the present disclosure. It should be noted that those skilled in the art may make improvements and modifications to the present disclosure without departing from the principle of the present disclosure. The improvements and modifications should also be included in the protection scope of the present disclosure. In addition, although some specific terms are utilized in this specification, the terms are described only for convenience of description and do not intended to limit the present disclosure.

What is claimed is:

1. A method for analyzing heart rate variability, comprising:
   1) acquiring electrocardiography data externally;
   2) performing a digitization process and a denoising process on the electrocardiography data;
   3) forming a sinus NN interval sequence with the processed electrocardiography data;
   4) selecting sinus NN interval data of a subject during a long term of more than 20 hours and during short terms of 2 to 10 minutes in an awake state and in a sleep state; and
   5) calculating at least one of a time domain index, a frequency domain index and a nonlinear index for the sinus NN interval data of the subject during the long term of more than 20 hours and during the short terms of 2 to 10 minutes in the awake state and in the sleep state, the calculation result are used to analyze the efficacy of vagus nerve stimulation (VNS) treatment for patients with medically intractable epilepsy, wherein the calculation formulas for time domain indexes are expressed as follows, and one or more of the following indexes are selected to be calculated during the analysis;

| Name of index | Definition of index | Unit |
|---|---|---|
| mean value (MEAN) | $MEAN = \overline{RR} = \sum_{i=1}^{N} RR_i / N$ | ms |
| overall standard deviation (SDNN) | $SDNN = \sqrt{\frac{1}{N}\sum_{i=1}^{N}(RR_i - \overline{RR})^2}$ | ms |
| root-mean-square of difference of adjacent interval (RMSSD) | $RMSSD = \sqrt{\frac{1}{N-1}\sum_{i=1}^{N-1}(RR_{i+1} - RR_i)^2}$ | ms |

-continued

| Name of index | Definition of index | Unit |
|---|---|---|
| percentage of adjacent intervals with difference greater than 50 ms (pNN50) | pNN50 = NN50/TotalNN × 100% | % | the calculation formulas for frequency domain indexes are expressed as follows, and one or more of the following indexes are selected to be calculated during the analysis;

| Name of index | Definition of index | Unit | Frequency range |
|---|---|---|---|
| TP | Total signal power, sum of VLF, LF and HF | $ms^2$ | ≤0.4 Hz |
| VLF | Power in very low frequency band | $ms^2$ | 0.0033 to 0.04 Hz |
| LF | Power in low frequency band | $ms^2$ | 0.04 to 0.15 Hz |
| HF | Power in high frequency band | $ms^2$ | 0.15 to 0.4 Hz |

-continued

| Name of index | Definition of index | Unit | Frequency range |
|---|---|---|---|
| LF/HF | Ratio of power in low frequency band to power in high frequency band | | | the nonlinear index comprises SD1 and SD2 indexes in a Poincare Plot, and one or more of the indexes are selected to be calculated during the analysis;

wherein the threshold of RMSSD is 37 ms, the threshold of pNN50 is 27%, the threshold of SD1 is 35 ms, and the threshold of HF is 798 ms.

2. The method for analyzing the heart rate variability according to claim 1, further comprising:

calculating one of RMSSD, pNN50, SD1 and HF.

3. The method for analyzing the heart rate variability according to claim 1, wherein a time period for the long term is set as 24 hours, and a time period for the short terms is set as 5 minutes.

* * * * *